US00PP20553P3

(12) United States Plant Patent
Dozier, Jr. et al.

(10) Patent No.: US PP20,553 P3
(45) Date of Patent: Dec. 15, 2009

(54) CHESTNUT PLANT NAMED 'AU GOBBLER II'

(50) Latin Name: *Castanea mollissima* Blume
Varietal Denomination: AU Gobbler II

(75) Inventors: W. Alfred Dozier, Jr., Opeika, AL (US); Joseph Daniel Norton, Auburn, AL (US); Curtis J. Hansen, Opelika, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/012,111

(22) Filed: Jan. 30, 2008

(51) Int. Cl.
*A01H 5/00* (2006.01)

(52) U.S. Cl. ..... Plt./152
(58) Field of Classification Search ..... Plt./152
See application file for complete search history.

(56) References Cited

PUBLICATIONS

Lin ye ke ji et al., "Forest Science & Technology", Jan. 1989, pp. 16–18, Baker Auxiliary Stacks SDI,. L56, No. 2–1990.
Crane, H.L. et al., Nut Breeding, U.S. Department of Agriculture Yearbook, Jan. 1937, pp. 837–837.
Hemming, E. Sam. "Chinese Chestnut In Maryland", Jan. 1944, pp. 32–34, A.R. Northern Nut Growers Assoc.
Kim, Kap Duk et al., Studies on the Farmers Cultivating Chestnut Orchards in Korea And Its Financial Analysis, Jan. 1971, pp. 51–74, Bull. Seol. Nut. Univ.Fores, No. 8.
Snare, Lester, Chestnuts Production, Jan. 1996, pp. 422–427, NSW Agriculture, Agfact H3.1.50., hhtp://www.ridc.gov.au/pub/handbook/chestnuts.pdf.
Harris, Hubert et al., Three Chinese Chestnuts: Au–Cropper, Au–Leadder, And Au–Homestead—Their History And Production, Mar. 1980, pp. 3–8, Agricultural Experiment Station Auburn University Circular 247.

*Primary Examiner*—Annette H Para
(74) *Attorney, Agent, or Firm*—Haverstock & Owens LLP

(57) ABSTRACT

'AU Gobbler II' is a new and distinct Chinese chestnut cultivar that is precocious and produces a medium to large crop annually of small nuts that mature early and start dropping about September 4. Nut drop continues for a 4 to 5 week period. The nuts mature and start dropping 2–3 weeks before most cultivars. The early nut drop and small nut size of 'AU Gobbler II' makes it ideal for use as a food source for turkey and other wildlife. 'AU Gobbler II' is an excellent companion cultivar to 'AU Gobbler I' as nut drop begins about 10 days after nut drop of 'AU Gobbler I' and extends the season of available food supply for wildlife. The major nut drop period of 'AU Gobbler II' occurs after the major nut drop period of 'AU Gobbler I'.

3 Drawing Sheets

Latin name of the genus and species of the plant claimed: *Castanea mollissima* Blume.

Variety denomination: 'AU Gobbler II'.

BACKGROUND OF THE INVENTION

A Chinese chestnut planting was established at Auburn University, Auburn, Ala., from nuts collected in China. The planting was established on the United States Department of Agriculture Horticulture Farm which in later years became the Mainstation Horticulture Farm. Precocious and prolific-bearing, blight resistant seedlings were selected for nut appearance, size and quality. Each generation of seedlings were the product of controlled mass pollination from the most promising seedlings selected from the previous generation. 'AU Cropper', 'AU Leader' and 'AU Homestead' were released from a second generation of approximately 2000 seedlings. A planting of third generation seedlings from controlled mass pollination of 'AU Leader', 'AU Homestead' and 'AU Cropper' was established at the Auburn University Piedmont Substation at Camp Hill, Ala.

SUMMARY OF THE INVENTION

'AU Gobbler II' is an open pollinated seedling of 'AU Leader'.

The present invention relates to a new and distinct Chinese chestnut cultivar that is precocious, produces a heavy crop annually, average nut size is small (5.7 g), begins nut drop about September 4 and continues for a 4 to 5 week period. The nuts mature and start dropping 2–3 weeks earlier than most chestnut cultivars. The large crop of small nuts is an excellent food source for turkey and other wildlife species. The small nut is ideal for consumption by turkey. Nut drop of 'AU Gobbler II' starts about 10 days after the beginning of nut drop from 'AU Gobbler I'. The two cultivars are excellent companion cultivars for a food source for turkey because they drop a large number of small nuts over an extended period of time. 'AU Gobbler I' is disclosed in U.S. patent application Ser. No. 12/012,030, filed on Jan. 30, 2008, and entitled "CHESTNUT PLANT NAMED 'AU GOBBLER I'", which is hereby incorporated by reference.

The new cultivar is able to be asexually reproduced by budding or grafting onto a seedling Chinese chestnut rootstock. The unique characteristics come true to form and are established and transmitted through asexual propagation.

DETAILED BOTANICAL DESCRIPTION

Figure 1:
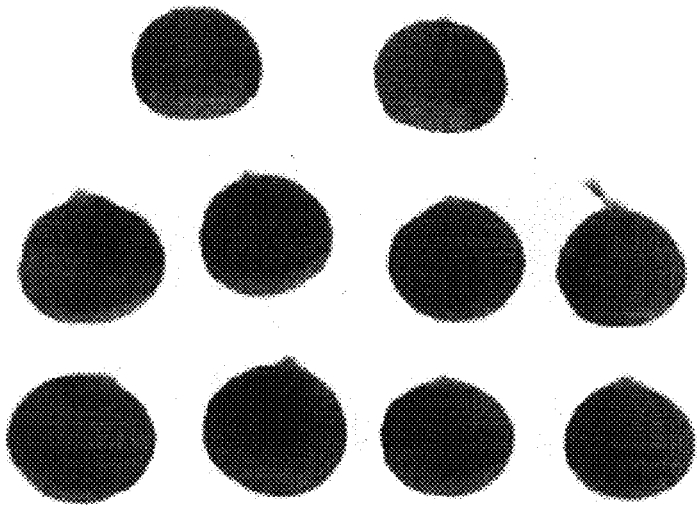
FIG. 1 is a photograph of nuts of the 'AU Gobbler II' cultivar.
Figure 2:
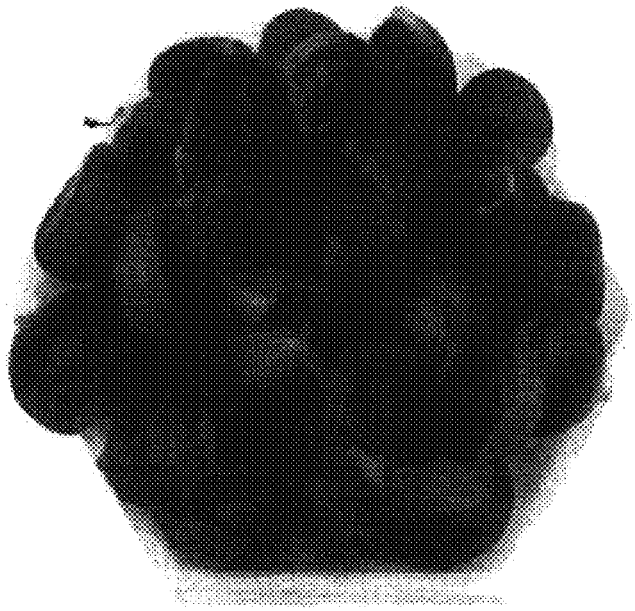
FIG. 2 is a photograph of nuts of the 'AU Gobbler II' cultivar.
Figure 3:
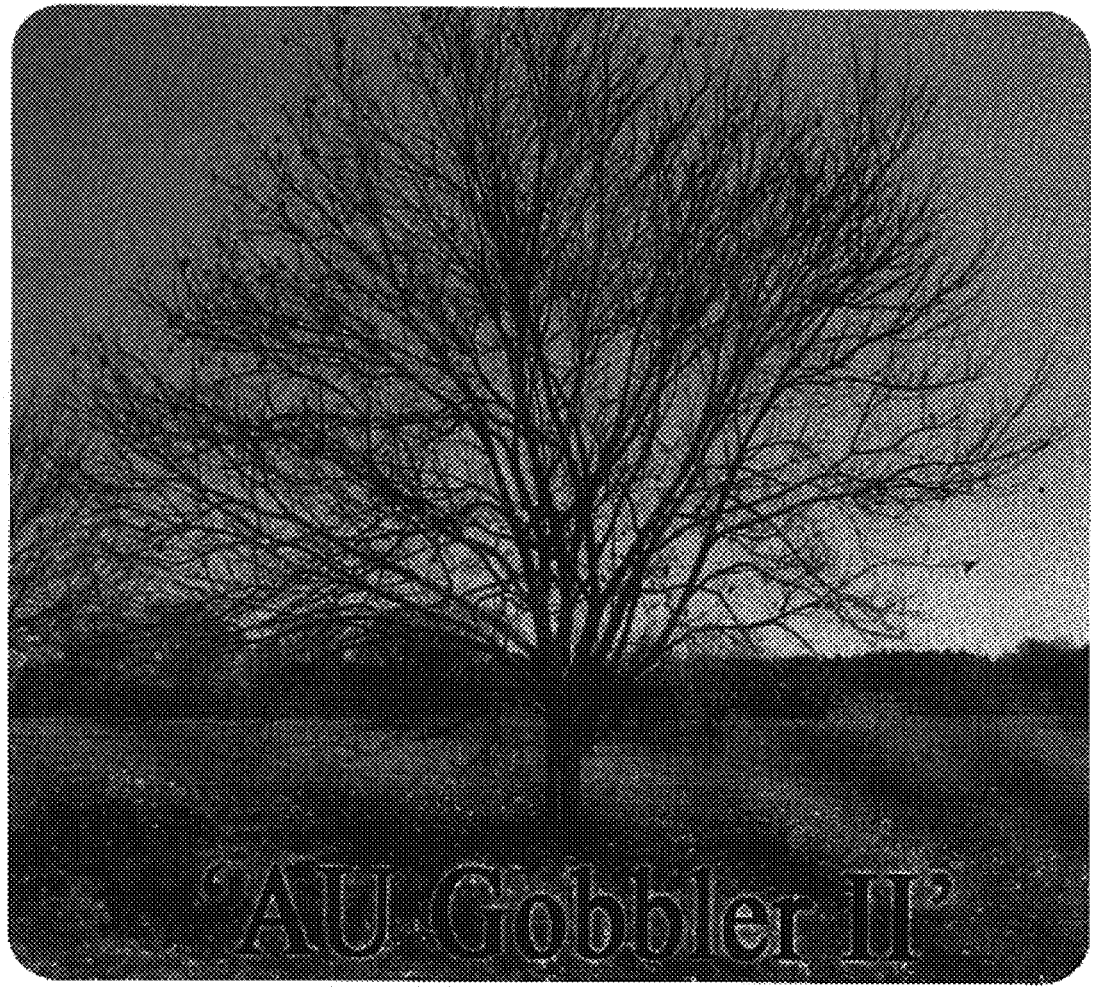
FIG. 3 is a photograph of a tree of the 'AU Gobbler II' cultivar.

The Chinese chestnut, *Castanea mollissima* Blume, is a cold hardy temperate zone species native to China. It can be grown between 30° and 50° latitudes. The Chinese chestnut is resistant to chestnut blight fungus *Cryphonectria parasitica*. Generally, Chinese chestnuts are grown on a wide range of soils, but well-drained, deep and fertile soils are considered the best. Soils should be slightly acidic with pH 5.6–6.5. The name *mollissima* means soft hair and this species is recognized by dense hair on young leaves and downy yellow terminal parts of the shoots in winter. The leaf blade is thicker, and, in general, mature leaves are broader than those of other species. The nuts have a small scar or hilum. The pellicle or thin membranous skin on the nuts is thin and peels readily from the kernel. The trees are spreading type and long-lived with a round top. The trees have bark with furrows and buds with 3–4 scales and leaves are 2 ranked, serrated with numerous parallel veins.

Chestnuts are monoecious and staminate flowers appear on erect cylindrical catkins with 10–20 stamens and 6-parted calyx. Pistillate flowers are borne on lower part of the upper staminate catkins and rarely on separate catkins usually 3 in a prickly symmetrical involucre with 7–9 styles and a 6-celled ovary. Nuts are small, brown with a pale scar at the base. Generally, 1–3 nuts per involucre or bur are present.

'AU Gobbler II' is a small round shaped tree. The branches are low, dense, and spreading. The original 15-year old 'AU Gobbler II' tree is 7.01 m tall, with a diameter at breast height of 26 cm, canopy width of 9.26 m and covers an area of 67.31 square meters. The nut is small and has a five year average weight of 5.7 grams. The nut length is 1.024 inches (26 mm) and the average nut width is 1.16 inches (29.4 mm). The nuts normally begin dropping about September 4, and nut drop continues for a 4 to 5 week period. The tree is very prolific, and fruits annually and starts dropping nuts about 2 to 3 weeks before most cultivars.

In the planting at the Piedmont Substation, Camp Hill, Ala., accurate yields could not be obtained due to extremely heavy wildlife (deer and turkey) feeding. Therefore, the trees were rated for crop load each year. 'AU Gobbler II' has been a producer of a medium to large crop load each season. In the fall of 2006, individual trees were caged with 6 foot (1.83 m) tall chicken wire prior to nut drop to exclude wildlife and nuts were picked up daily from the beginning through completion of nut drop. The original 15-year old 'AU Gobbler II' tree produced 107 pounds (48.64 kg) of nuts in 2006. This yield is above the reported yields for similar aged trees. It is a prolific and annual producer.

The table below illustrates the specific differences between the 'AU Gobbler II' cultivar and the 'Revival' cultivar.

The botanical details of this new and distinctive variety of chestnut tree - with color definitions (except those in common color terms) referenced to Royal Horticultural Society's Colour Chart (RHS) and color was also determined using an electronic spectrophotometer to determine hue angle and chroma (spectrophotometer model CM-2002; Minolta Camera Co, Japan).

'AU GOBBLER II' CHESTNUT

Tree:

Size (at maturity) - small - fifteen year old original tree is 7.01 meters tall with a canopy width of 9.26 meters and a canopy area of 67.31 sq. meters
Tree shape is round with low, dense and spreading branches.
Vigor - vigorous Trunk:

Form - upright with branches low, dense and spreading.
Texture- relatively smooth
Color of bark - brown, RHS N200B, Chroma C* 9.56 hue angle 81.38.

Branches:

Form - spreading
Texture - relatively smooth
Lenticels - few, small
Branching habit - low and dense, spreading
Color - new wood: brown, RHS N200A, Chroma C* 11.42, hue angle 76.0; mature wood: greyed-green, RHS 197A, Chroma C* 13.55, hue angle 92.44

Foliage:

Quantity - abundant
Density - dense

Leaves:

Size - large. Length (cm) 18.4 (13.6-25.5) [20]
width (cm) 7.5 (5.4-9.8) [20]
leaf ratio 2.5 (2.0-3.2) [20]
Shape - broadly elliptic
leaf tip- acuminate
leaf base- rounded to broadly cuneate
Thickness- thick. Leaf venation 1° pinnate: 2° ± parallel, strongly prominent abaxially
Texture - coriaceous (thick)
Margin - coarsely serrate with large spreading to ascending teeth
Petiole - length (cm) 1.0 (0.6-1.3) [20]
Petiole pubescence- glabrous to sparsely hairy
Color - adaxial surface, glabrous blade, glabrous to sparsely hairy veins, dark green, RHS 147A Chroma C* 10.40, hue angle 124.04
abaxial surface, weakly to moderately hairy, with stellate hairs on blade; veins sparsely pubescent, light green, RHS 148B, Chroma C* 18.89 hue angle 109.49

Bloom:

Amount of bloom - heavy
Color - at anthesis, RHS 161D greyed-yellow group, RHS 157D green-white group, RHS155C white group
Blooming period - mid-May. After foliation in April.
Age at which tree starts flowering - early, 2-3 years after planting grafted tree.
Male flower - Catkin length (cm) - 15.3 (9.9-19.6) [10]
Male flower - stamen number per catkin - 9.8 (8-11) [10]
Female flower - flower number per bur - 4.0
Female flower - style number per flower 7.9 (7-9) [12]

Crop:

Bearing - regular annual bearer
Productivity - prolific
Ripening period - long, nuts begin dropping about September 5 and continues for a 4-5 week period.
Distribution of nuts on tree - well distributed, fruits on terminals with 2-4 burs per terminal.
Tenacity - burs crack while on tree and nuts release and drop from bur.

Hull:

Description - spiny, round bur
Size - 1.82"-2.14" in diameter

-continued

Number of nuts - 2-3 per bur
Dehiscence - splits easily when still on tree
Color - yellow-green at dehiscence, RHS N144C
Nut:

Size - small; average size - 1.02" × 1.16" × 0.62". Average weight - 5.7 grams - (65-101) nuts per pound.
Form - flattened on 1 side, occ. 2; mostly hemispheric on other side; broadly rounded basally; rounded apically with a little or no tip.
Blossom end - little or no tip
Basal end - flattened
Color - dark brown, lustrous; RHS 200B, Chroma C* 15.12, hue angle 42.50
Pubescence - mixed long and short, fine, white hairs densely covering the distal ⅛ end of nut, otherwise sparse to glabrous elsewhere
Shell - thin
Hardness of shell - relatively hard, yet not rigid
Texture of shell - smooth
Percentage of kernel to nut - very high-90-95%
Kernel:

Size - almost as large as nut size
Form - same as nut shape
Pellicle - thin
Flavor - excellent, very sweet
Color - light straw color, RHS 162A, Chroma C* 51.84, hue angle 82.23.
Resistance to insects: no unusual susceptibilities noted
Resistance to disease: no susceptibilities to disease noted
The chestnut tree and its nuts herein described may vary in slight detail due to climatic and soil conditions under which the variety may be grown; the present description being of the variety as grown in Camp Hill, Ala.

The botanical details of this variety of chestnut tree - with color definitions (except those in common color terms) referenced to Maerz and Paul Dictionary of Color - are as follows:
'REVIVAL'

Tree:

Size (at maturity) - large
Vigor - very vigorous
Trunk:

Form - upright with branches spreading in upper reaches of tree.
Texture - relatively smooth
Color of bark - Silvergray (13-A-1)
Branches:

Form - strong
Texture - relatively smooth
Lenticels - few, small
Branching habit - spreading in upper region of tree
Color- new wood: reddish brown and glossy, mature wood: silver gray
Foliage:

Quantity - abundant
Density - dense
Leaves:

Size - large. Average length - 5.7" (including petiole).
Average width - 2"
Shape - oblong with acute tip and rounded base
Thickness - thick
Texture - smooth
Margin - dentate
Petiole - length: medium Thickness: medium.
Color - Top side - glossy dark green (22-L-12).
Under side - lighter green (21-D-7).
Bloom:

Amount of bloom - heavy
Color - cream white (17-B-1)
Blooming period - late. After leaf out in April -continued Age at which tree starts flowering - early; 2-3 years years after graft replacement
Crop:

Bearing - regular (yearly) bearer
Productivity - prolific
Ripening period - short. September 15-October 1.
Distribution of nuts on tree - well distributed
Tenacity - burrs crack while on tree and nuts easily release, many falling by themselves
Hull:

Description - spiny, round burr
Size - 3-4" in diameter
Number of nuts - 2-3 per burr
Dehiscence - splits easily when still on tree. Some entire burrs split and fall to ground
Color - brown (15-A-8)
Nut:

Size - large. Average size - 1⅛" × 1⅛" × 1" thick.
Average weight - 24-32 nuts per pound
Form - broad and ovoid on one side, flat on other side
Blossom end - pointed tip
Basal end - flattened
Color - India Red (7-L-6).
Shell - thin
Hardness of shell - relatively hard, yet not rigid
Texture of shell - smooth
Percentage of kernel to nut - very high (95%)
Kernel:

Size - almost as large as nut size
Form - same as nut shape
Pellicle - thin
Flavor - excellent. Very sweet.
Color - Oyster white (10-B-1)
Resistance to insects: no unusual susceptibilities noted
Resistance to disease: very high inherent resistance to chestnut bark fungus (*Endothia parasitica*), no other susceptibilities to any other disease
The chestnut tree and its nuts herein described may vary in slight detail due to climatic and soil conditions under which the variety may be grown; the present description being of the variety as grown in Alachua, Fla.

'AU Buck I' is different from 'AU Gobbler II' in several ways. For example, the trees, the trunk colors, the branch colors, the leaves, the crop and the nuts have differences. Specifically, the 'AU Buck I' tree is taller with a canopy width and canopy area smaller than the 'AU Gobbler II' tree. The 'AU Buck I' branches are grey-brown; whereas, the 'AU Gobbler II' branches are brown (new) or greyed-green (mature). The leaves differ in size, shape, texture, margin and color. The ripening period for the 'AU Buck I' is around August 28 and continues for a 4–5 week period, but the 'AU Gobbler II' ripening period is around September 4 or 5 and continues for 4–5 weeks. The average weight of the nuts of 'AU Buck I' is 9.3 grams versus 5.7 grams for 'AU Gobbler II'. Furthermore, 'AU Buck I' has roughly 49 nuts per pound, and 'AU Gobbler II' has roughly 65–101 nuts per pound.

'AU Buck II' is different from 'AU Gobbler II' in several ways. For example, the trees, the trunk colors, the branch colors, the leaves, the crop and the nuts have differences. Specifically, the 'AU Buck II' tree is taller with a canopy width and canopy area larger than the 'AU Gobbler II' tree. The 'AU Buck II' branches are brown (new) or grey-brown (mature); whereas the 'AU Gobbler II' branches are brown (new) or greyed-green (mature). The leaves differ in size, shape, margin and color. The ripening period for the 'AU Buck II' is around September 14 and continues for a 4–5 week period, but the 'AU Gobbler II' ripening period is around September 4 or 5 and continues for 4–5 weeks. The average weight of the nuts of 'AU Buck II' is 16.6 grams versus 5.7 grams for 'AU Gobbler II'. Furthermore, 'AU Buck II' has roughly 27 nuts per pound, and 'AU Gobbler II' has roughly 65–101 nuts per pound.

'AU Buck III' is different from 'AU Gobbler II' in several ways. For example, the trees, the trunk colors, the branch colors, the leaves, the crop and the nuts have differences. Specifically, the 'AU Buck III' tree is shorter with a canopy width and canopy area smaller than the 'AU Gobbler II' tree. The 'AU Buck III' branches are brown (new) or grey-brown (mature); whereas, the 'AU Gobbler II' branches are brown (new) or greyed-green (mature). The leaves differ in size, shape and color. The ripening period for the 'AU Buck III' is around September 25 and continues for a 4–5 week period, but the 'AU Gobbler II' ripening period is around September 4 or 5 and continues for 4–5 weeks. The average weight of the nuts of 'AU Buck III' is 10.9 grams versus 5.7 grams for 'AU Gobbler II'. Furthermore, 'AU Buck III' has roughly 42 nuts per pound, and 'AU Gobbler II' has roughly 65–101 nuts per pound.

'AU Buck IV' is different from 'AU Gobbler II' in several ways. For example, the trees, the trunk colors, the branch colors, the leaves, the crop and the nuts have differences. Specifically, the 'AU Buck IV' tree is taller with a canopy width and canopy area smaller than the 'AU Gobbler II' tree. The 'AU Buck IV' branches are grey-brown (new) or greyed-green (mature); whereas, the 'AU Gobbler II' branches are brown (new) or greyed-green (mature). The leaves differ in size, shape margin and color. The ripening period for the 'AU Buck IV' is around October 10 and continues for a 5–6 week period, but the 'AU Gobbler II' ripening period is around September 4 or 5 and continues for 4–5 weeks. The average weight of the nuts of 'AU Buck IV' is 15.5 grams versus 5.7 grams for 'AU Gobbler II'. Furthermore, 'AU Buck IV' has roughly 29 nuts per pound, and 'AU Gobbler II' has roughly 65–101 nuts per pound.

'AU Premier' is different from 'AU Gobbler II' in several ways. For example, the size of the trees, the branches, the leaves, the crop and the nuts have differences. Specifically, the 'AU Premier' tree is shorter with a canopy width and a canopy area smaller than the 'AU Gobbler II' tree. The 'AU Premier' branches are strong; whereas, the 'AU Gobbler II' branches are spreading. The leaves differ in size, shape, thickness, texture, margin and color. The ripening period for the 'AU Premier' is early September through mid-November, but the 'AU Gobbler II' ripening period is around September 4 or 5 and continues for 4–5 weeks. The average weight of the nuts of 'AU Premier' is 1.26 grams versus 5.7 grams for 'AU Gobbler II'. Furthermore, 'AU Premier' has roughly 360.3 nuts per pound, and 'AU Gobbler II' has roughly 65–101 nuts per pound.

'AU Encore' is different from 'AU Gobbler II' in several ways. For example, the size of the trees, the branches, the leaves, the crop and the nuts have differences. Specifically, the 'AU Encore' tree is shorter with a canopy width and a canopy area smaller than the 'AU Gobbler II' tree. The 'AU Encore' branches are strong; whereas, the 'AU Gobbler II' branches are spreading. The leaves differ in size, shape, thickness, texture, margin and color. The ripening period for the 'AU Encore' is late September through late November, but the 'AU Gobbler II' ripening period is around September 4 or 5 and continues for 4–5 weeks. The average weight of the nuts of 'AU Encore' is 2.4 grams versus 5.7 grams for 'AU Gobbler II'. Furthermore, 'AU Encore' has roughly 189.2 nuts per pound, and 'AU Gobbler II' has roughly 65–101 nuts per pound.

What is claimed is:

1. A new and distinct cultivar of the species *Castanea mollissima* Blume named 'AU Gobbler II' as described and illustrated herein.

* * * * *

'AU Gobbler II'

'AU Gobbler II'

UNITED STATES PATENT AND TRADEMARK OFFICE

CERTIFICATE OF CORRECTION

PATENT NO. : PP 20,553 P3
APPLICATION NO. : 12/012111
DATED : December 15, 2009
INVENTOR(S) : Dozier, Jr. et al.

It is certified that error appears in the above-identified patent and that said Letters Patent is hereby corrected as shown below:

ON THE TITLE PAGE

Title Page, Item (75) Inventors, please replace "Opeika" with "Opelika" so that the first line of the field correctly reads:

Item -- (75) Inventors: W. Alfred Dozier, Jr., Opelika, AL (US); --

Please add Item (65) Prior Publication Data so that the field correctly reads:

Item -- (65) Prior Publication Data
US 2009/0229023 P1 Sep. 10, 2009 --

Signed and Sealed this

Twenty-sixth Day of January, 2010

David J. Kappos

David J. Kappos
*Director of the United States Patent and Trademark Office*